(12) United States Patent
Govari et al.

(10) Patent No.: US 10,912,473 B2
(45) Date of Patent: Feb. 9, 2021

(54) ROUTING OF ANALOG SIGNALS USING ANALOG/DIGITAL FOLLOWED BY DIGITAL/ANALOG CONVERSION

(71) Applicant: BIOSENSE WEBSTER (ISRAEL) LTD., Yokneam (IL)

(72) Inventors: Assaf Govari, Haifa (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 368 days.

(21) Appl. No.: 15/949,288

(22) Filed: Apr. 10, 2018

(65) Prior Publication Data

US 2019/0307348 A1  Oct. 10, 2019

(51) Int. Cl.
| | | |
|---|---|---|
| *A61B 5/04* | (2006.01) |
| *A61B 5/042* | (2006.01) |
| *A61B 5/0428* | (2006.01) |
| *A61B 5/0432* | (2006.01) |
| *A61B 5/00* | (2006.01) |
| *A61B 5/044* | (2006.01) |
| *A61B 5/0402* | (2006.01) |
| *H03M 1/12* | (2006.01) |
| *H03M 1/66* | (2006.01) |

(52) U.S. Cl.
CPC .......... *A61B 5/04017* (2013.01); *A61B 5/042* (2013.01); *A61B 5/0402* (2013.01); *A61B 5/044* (2013.01); *A61B 5/0428* (2013.01); *A61B 5/0432* (2013.01); *A61B 5/7228* (2013.01); *H03M 1/1205* (2013.01); *H03M 1/66* (2013.01)

(58) Field of Classification Search
CPC ... A61B 5/04017; A61B 5/0402; A61B 5/042; A61B 5/0428; A61B 5/0432; A61B 5/044; A61B 5/7228; H03M 1/1205; H03M 1/66
See application file for complete search history.

(56) References Cited

U.S. PATENT DOCUMENTS

| | | | |
|---|---|---|---|
| 4,360,030 A * | 11/1982 | Citron | A61B 5/0432 600/515 |
| 4,920,969 A | 5/1990 | Suzuki et al. | |
| 5,090,418 A | 2/1992 | Squires et al. | |

(Continued)

OTHER PUBLICATIONS

European Search Report for corresponding EPA No. 19168171.7 dated Aug. 22, 2019.

(Continued)

*Primary Examiner* — Lindsey G Wehrheim

(57) ABSTRACT

An apparatus includes analog-to-digital conversion (ADC) circuitry, digital processing logic, and digital-to-analog conversion (DAC) circuitry. The ADC circuitry is coupled to digitize multiple analog input signals so as to generate digital samples. The digital processing logic is configured to extract, from the digital samples, one or more first digital signals corresponding to a first selected subset of the analog input signals, and one or more second digital signals corresponding to a second selected subset of the analog input signals. The digital processing logic is further configured to output the one or more first digital signals to a digital medical instrument. The DAC circuitry is coupled to convert the one or more second digital signal into one or more analog output signals, and to output the one or more analog output signals to an analog medical instrument.

18 Claims, 2 Drawing Sheets

(56) References Cited

U.S. PATENT DOCUMENTS

| | | |
|---|---|---|
| 5,126,967 A | 6/1992 | Simko |
| 5,503,159 A | 4/1996 | Burton |
| 6,825,875 B1 | 11/2004 | Strub et al. |
| 2006/0161068 A1 | 7/2006 | Hastings et al. |
| 2013/0213399 A1 | 8/2013 | Hansmann |
| 2016/0166171 A1 | 6/2016 | Warner |

OTHER PUBLICATIONS

Jari Nurmi et al., "An Integrated Sensor Interface for ECG Measurements", Compeuro, May 8, 1989, pp. 3/164-3/166.

* cited by examiner

ROUTING OF ANALOG SIGNALS USING ANALOG/DIGITAL FOLLOWED BY DIGITAL/ANALOG CONVERSION

FIELD OF THE INVENTION

The present invention relates generally to apparatus and methods for signal-processing in medical instruments, and particularly to adapters for transmitting electrocardiogram (ECG) signals.

BACKGROUND OF THE INVENTION

Electrocardiography (ECG) is a well-established cardiac diagnostic technique. Various techniques are known in the art for transferring and recording ECG signals. For example, U.S. Pat. No. 4,920,969 describes an ambulatory physiological evaluation system where information from ECG electrodes is recorded on a portable cassette recorder. After the information has been recorded over a desired period of time, the information is presented, through an interface and an analog to digital converter, to the memory of a standalone computer located in a hospital or office. The computer calculates such items as R-R time intervals, electrocardiogram and time-activity curves, and displays these items and other physiological data. From the calculations made by the computer, average heart rate, number of aberrant beats and other values of physiological significance may be calculated for a time interval of interest.

As another example, U.S. Patent Application Publication 2006/0161068 describes an ECG electrode system that includes the use of electrodes adapted to attach to the body via suction. Embodiments allows for any analog recorder/monitor to be directly connected to the ECG electrode system of the present invention. In an embodiment, the signal is never digitized, thus the signal can be sent directly to an analog recorder/monitor where the signal can be displayed. In addition, routing various analog signals coming from electrodes to several or one analog to digital converters is provided. The analog to digital converters can then feed the digital signals that result to any digital ECG recorder or monitor. Thus, the system is adaptable to be used with any analog or digital recorder/monitor.

As yet another example, U.S. Pat. No. 5,090,418 describes a time saving automatic screening system for detection, measurement, analysis and plotting of ECG signals employing arrhythmia analysis programs on long term ambulatory (Holter) recordings to assess the ECG signals and categorize the recorded data. The method and apparatus disclosed make it possible to identify and screen out entire long term (Holter) ECG recordings containing no significant abnormalities in the hearts arrhythmia or the beat morphology. Thus, the cost of Holter scanning is greatly reduced by reserving for manual scanning only those recordings that contain significant abnormalities in the hearts arrhythmia or the beat morphology. In the preferred embodiment, three high speed A/D convertors are used to convert three channels of analog ECG data into three digital channels.

SUMMARY OF THE INVENTION

An embodiment of the present invention provides an apparatus including analog-to-digital conversion (ADC) circuitry, digital processing logic, and digital-to-analog conversion (DAC) circuitry. The ADC circuitry is coupled to digitize multiple analog input signals so as to generate digital samples. The digital processing logic is configured to extract, from the digital samples, one or more first digital signals corresponding to a first selected subset of the analog input signals, and one or more second digital signals corresponding to a second selected subset of the analog input signals. The digital processing logic is further configured to output the one or more first digital signals to a digital medical instrument. The DAC circuitry is coupled to convert the one or more second digital signal into one or more analog output signals, and to output the one or more analog output signals to an analog medical instrument.

In some embodiments, the second selected subset includes ECG signals, and the first selected subset includes non-ECG signals.

In some embodiments, the apparatus further includes an output connector, which is configured to receive an input connector of the analog medical instrument so as to convey the one or more analog output signals to the analog medical instrument.

In an embodiment, the second selected subset includes analog ECG signals, and the analog medical instrument includes an analog ECG recording instrument.

In another embodiment, the ADC circuitry, the digital processing logic and the DAC circuitry are integrated on a single circuit board.

In some embodiments, the multiple analog input signals are frequency-multiplexed onto respective carrier frequencies.

There is additionally provided, in accordance with an embodiment of the present invention, a method, including digitizing multiple analog input signals so as to generate digital samples. One or more first digital signals corresponding to a first selected subset of the analog input signals, and one or more second digital signals corresponding to a second selected subset of the analog input signals, are extracted from the digital samples. One or more first digital signals are outputted to a digital medical instrument. One or more second digital signals are converted into one or more analog output signals, and the one or more analog output signals are outputted to an analog medical instrument.

There is also provided, in accordance with an embodiment of the present invention, an apparatus, including analog-to-digital conversion (ADC) circuitry, digital processing logic, and digital-to-analog conversion (DAC) circuitry. The ADC circuitry is coupled to digitize multiple analog input signals so as to generate digital samples. The digital processing logic is configured to split the digital samples into first and second identical copies, and output the second copy of the digital signals. The DAC circuitry, which includes a digital filter and is coupled to filter the second copy of the digital input signals, to convert the filtered second copy into one more analog output signals, and to output the one or more analog output signals to an analog medical instrument.

There is further provided, in accordance with an embodiment of the present invention, a method, including digitizing multiple analog input signals so as to generate digital samples. The digital samples are split into first and second identical copies. The first copy of the digital signals is sent to a digital medical instrument. The second copy of the digital input signals is filtered by a digital filter. The filtered second copy is converted into one more analog output signals, and the one or more analog output signals are outputted to an analog medical instrument.

The present invention will be more fully understood from the following detailed description of the embodiments thereof, taken together with the drawings in which:

DETAILED DESCRIPTION OF EMBODIMENTS

Overview

Sensors fitted to catheters, such as ECG sensors, contact-force sensors and position sensors, typically generate modulated analog signals. In various medical systems, multiple modulated analog signals such as exemplified above are routed to a console, in which the modulated analog signals are converted to digital signals to undergo further signal processing.

In many occasions, however, at least some of the analog signals, such as analog ECG signals sensed in a heart, need to be maintained in the form of analog signals, so as to be recorded, for example, by a legacy analog ECG recording instrument.

Embodiments of the present invention that are described herein provide a routing circuity for conveying analog signals to analog medical instruments, such as legacy analog ECG recording instruments. In some embodiments, the disclosed routing circuity receives multiple analog signals modulated about different carrier frequencies (i.e., frequency multiplexed). A wideband analog-to-digital converter (ADC) in the routing circuitry digitizes (i.e., converts) the modulated analog input signals so as to generate digital samples (e.g., into a wideband digital signal) and outputs the digital samples to a digital processing logic. The digital processing logic extracts from the digital samples one or more first digital signals corresponding to a first selected subset of the analog input signals. Furthermore, the digital processing logic extracts one or more second digital signals corresponding to a second selected subset of the analog input signals.

In some embodiments, the digital processing logic outputs the one or more first digital signals to a digital medical instrument, and outputs the one or more second digital signals to a digital-to-analog converter (DAC). The DAC converts the one or more second digital signal into one or more analog output signals, and outputs the one or more analog output signals to an analog medical instrument. In an embodiment, the multiple analog signals comprise one or more analog ECG signals. The received analog ECG signals are digitized so as to generate digital samples, which are extracted and output to the ADC that converts the digital ECG samples to one or more corresponding analog ECG signals that serve as inputs to an analog ECG recording instrument.

The disclosed routing circuity provides a simple yet effective means for connecting to legacy medical instruments.

System Description

Figure 1:
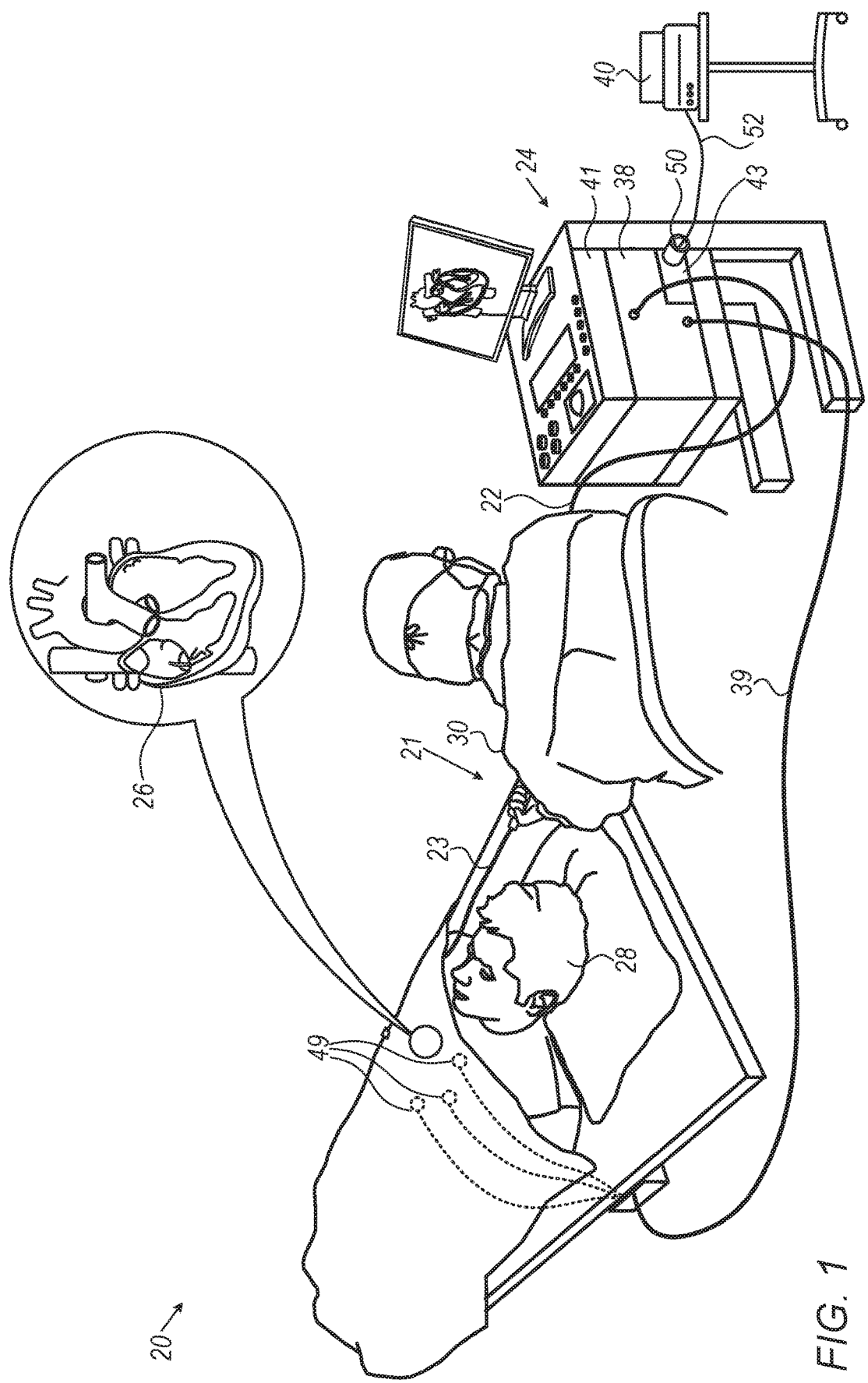
FIG. 1 is a schematic, pictorial illustration of a catheter-based electro-anatomical sensing system coupled to an analog ECG recording instrument, in accordance with an embodiment of the present invention.

FIG. 1 is a schematic, pictorial illustration of a catheter-based electro-anatomical sensing system 20 coupled to an analog ECG recording instrument 40, in accordance with an embodiment of the present invention. System 20 comprises a catheter 21, wherein a shaft 22 of the catheter is inserted into a heart 26 of a patient 28 through a sheath 23. The proximal end of catheter 21 is connected to a console 24.

Console 24 comprises interface circuits 38 for receiving signals from catheter 21 and/or signals from external sensors, such as from sensors attached to the patient skin. In the embodiment described herein, catheter 21 may be used for any suitable diagnostic purposes, such as electrophysiological mapping of heart 26.

A physician 30 inserts shaft 22 through the vascular system of patient 28. Physician 30 navigates the distal end of shaft 22 to a target location in heart 26. Once the distal end of shaft 22 has reached the target location, physician 30 retracts sheath 23, letting one or more sensors fitted at a distal end of shaft 22 collect and/or inject one or more signals.

Console 24 comprises a processor 41, typically a general-purpose computer, with suitable front end and interface circuits 38 for receiving ECG signals as well as non-ECG signals (such as position signals) from sensing-electrodes fitted at a distal end of shaft 22, and/or from external-electrodes 49, which are typically placed around the chest of patient 26. For this purpose, processor 41 is connected to the sensing-electrodes via wires running within shaft 22, and to external-electrodes 49 by wires running through a cable 39.

As noted above, console 24 receives multiple analog signals from electrodes 49 and/or the sensors fitted at the distal end of shaft 22, such as the ECG signals, location signals, and contact force signals, for example. Thus, as indicated above, analog ECG signals cannot be easily separated and routed directly to analog ECG recording instrument 40. Rather, a routing circuitry (seen in FIG. 2) inside console 24 digitizes all the analog signals that shaft 22 and/or cable 39 conveys, so console 24 can process an all digitized data. The routing circuitry further extracts the digitize ECG signals from the digitized signals. In order to output the ECG signals, the routing circuitry converts the extracted digitalized ECG signals back to analog signals and transmit the later to analog ECG recording instrument 40 via a cable 52 connected to an analog output connector 50 of the routing circuitry.

In some embodiments, the routing circuitry may be an integral part of console 24 circuitry. In other embodiments the routing circuitry may be integrated into console 24 in an adapter case 43.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Although the pictured embodiment relates specifically to an ECG and position sensing system, the elements of system 20 and the methods described herein may alternatively be applied to other sorts of multi-electrode sensing and/or with systems that operate additional devices, such as ablation devices.

Routing of Analog Signals Using A/D Followed By D/A Conversion

Figure 2:
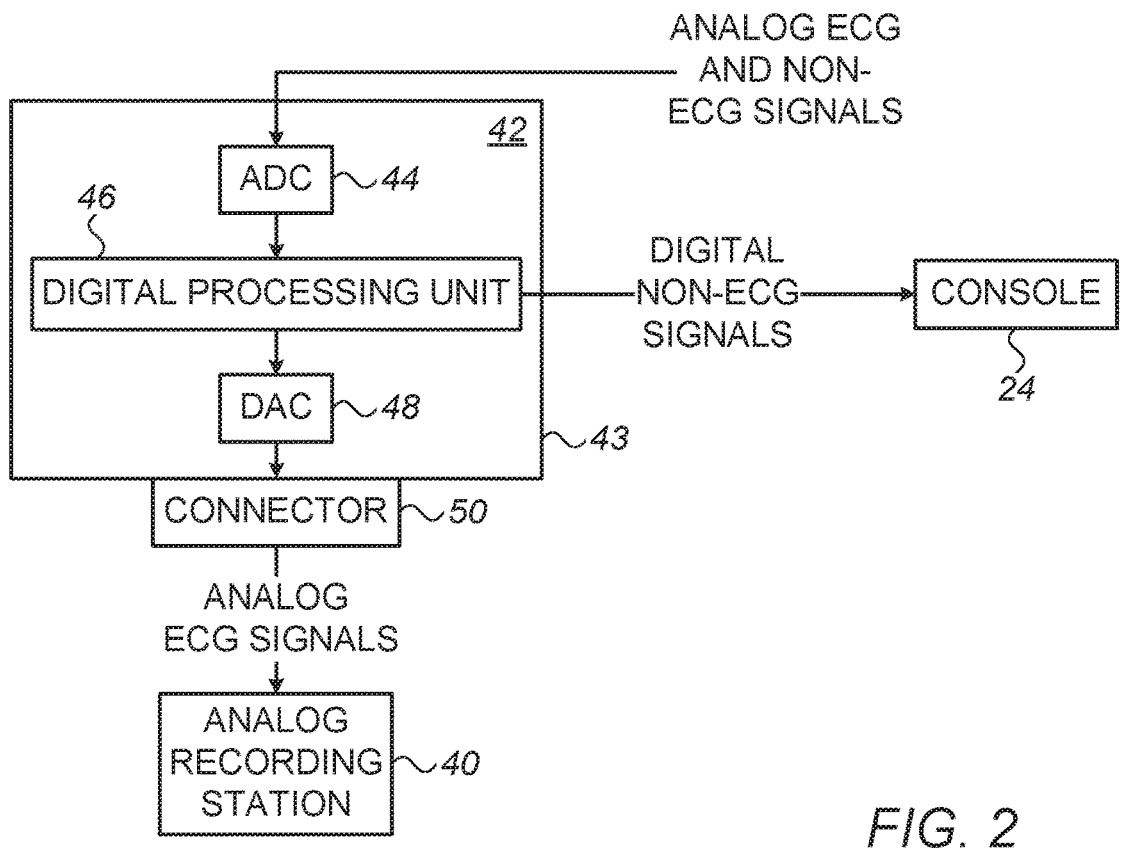
FIG. 2 is a block diagram that schematically illustrates a routing circuitry, in accordance with an embodiment of the present invention.

FIG. 2 is a block diagram that schematically illustrates routing circuitry 42, in accordance with an embodiment of the present invention. In the exemplified configuration, a plurality of modulated analog signals is received into routing circuitry 42 inside a case 43 and is digitized by a wideband analog-to-digital converter (ADC) 44. The analog signals comprise ECG signals as well as non-ECG analog signals, such as position signals and contact force signals. Typically, the received analog input signals comprise continuous-time signals modulated about different carrier frequencies (i.e., frequency multiplexed), and ADC 44 is configured to convert these modulated analog input signals into a wideband digital signal.

In an embodiment, a digital processing unit 46 (also referred to as digital processing logic) inside routing circuitry 42 extracts digital ECG signals from the wideband digital signal, and outputs the digital ECG signals to a digital-to-analog converter (DAC) 48. The non-ECG digital signals are output by unit 46 to various circuits in console 24, which are not depicted for simplicity of FIG. 2. DAC 48 converts the extracted digital ECG signals into analog ECG signals and outputs the analog signals to an output connector 50 fitted to case 43. Output connector 50 is configured to accept a cable from a legacy analog ECG recording instrument, such as cable 52 seen in FIG. 1 connected to a standalone analog ECG recording station 40.

In an embodiment, ADC 44, processing unit 46 and DAC 48 are all integrated on a single printed circuit board. The various elements of routing circuitry 42 may be implemented in hardware, e.g., using one or more discrete components, Field-Programmable Gate Arrays (FPGAs) or Application-Specific Integrated Circuits (ASICs). In some embodiments, some elements of routing circuitry 42, e.g., processing unit 46, may be implemented in software, or using a combination of software and hardware elements. The configuration of routing circuitry 42 shown in FIG. 2 is an example configuration, which is depicted purely for the sake of conceptual clarity. In alternative embodiments, routing circuitry 42 may be implemented using any other suitable components or configuration.

In an alternative embodiment, an external box, rather than DAC 48 within routing circuitry 42, is used for the conversion of the digitized ECG signals into analog ones. In such a case, digital processing unit 46, or an alternative unit—such as a digital signal splitter —splits the digital samples into first and second identical copies. Unit 46 sends the first copy of the digital signals to a digital medical instrument (e.g., to various circuits in console 24). Unit 46 outputs the second copy of the digital signals (i.e., both ECG subset and non-ECG subset of digital signals) to an external box comprising DAC 48, rather than digital processing unit 46 splitting the digital signals to non-ECG and ECG signals.

The digital signals are transmitted using a cable connection or a wireless connection and the external box, which includes a unit such as DAC 48, comprises circuitry that filters the received second copy of the digital signals so as to retain only a first subset of the digital input signals (e.g., the ECG subset of digital signals), while dropping a second subset of the digital input signals (e.g., the non-ECG subset of digital signals). Then, DAC 48 converts the ECG signals from digital to analog, and outputs the one or more analog output signals, such as analog ECG signals, to an analog medical instrument, such as analog recording station 40. By applying such an architecture, the system may achieve lower pickup noise relative to sending the ECG signals as analog signals to external analog recording station 40. By maintaining the signals in digital form, the signals can be filtered to remove various types of noise added during transmission to station 40 (e.g., noise at 50 Hz/60 Hz and their higher harmonics) before converting the ECG signals to analog.

Figure 3:
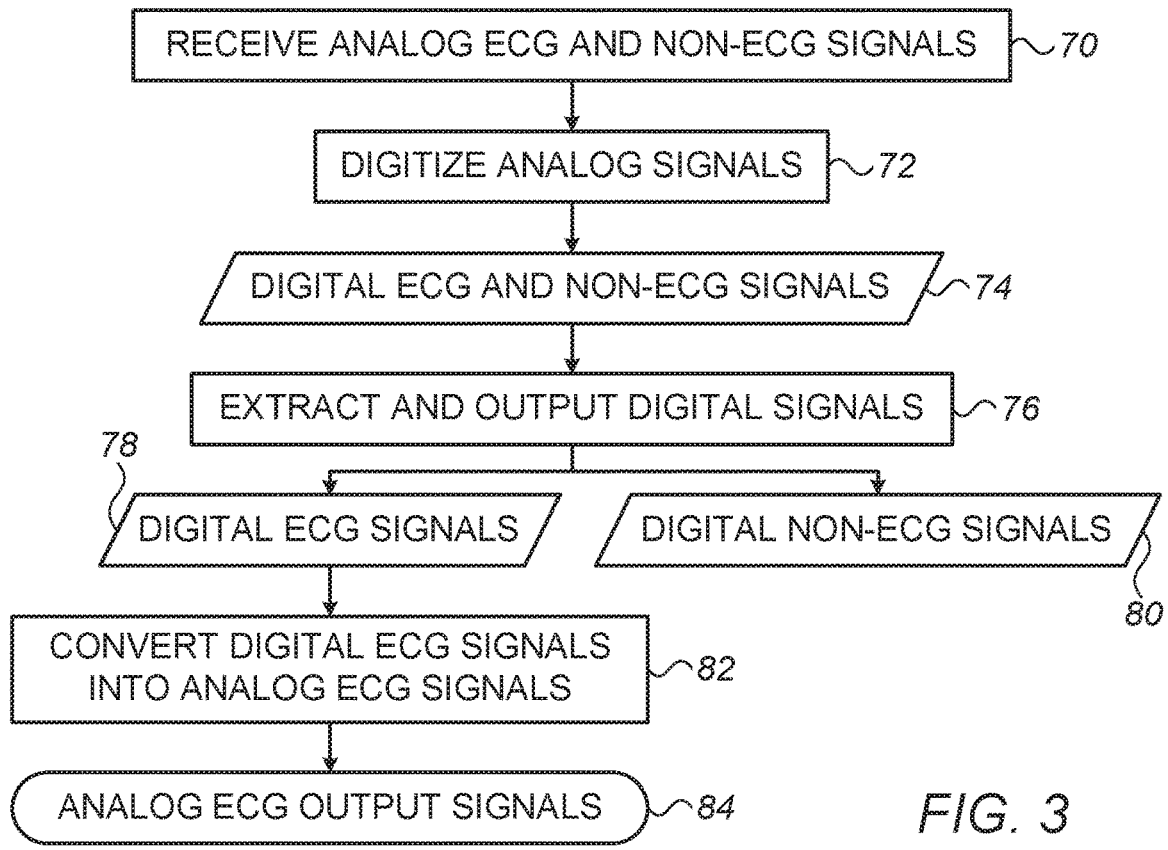
FIG. 3 is a flow chart that schematically illustrates a method for signal processing in a routing circuitry, in accordance with an embodiment of the present invention.

FIG. 3 is a flow chart that schematically illustrates a method for signal processing in an analog routing circuitry, in accordance with an embodiment of the present invention. As seen, analog ECG and non-ECG analog signals are received at routing circuitry 42, at a receiving step 70. ADC 44 converts all the received analog signals into digital ECG and non-ECG signals 74, at an ADC step 72. Subsequently, digital processing unit 46 extracts from the digital signals digital ECG digital signals 78, and non-ECG digital signals 80, at an extracting step 76, as described above. DAC 48 then converts the extracted an outputted digital ECG signals into analog output signals 84, at a DAC step 82. DAC 48 then transmits analog ECG signals 84 to a legacy ECG recording instrument 40, as elaborated above.

The example configurations shown in the figures are chosen purely for the sake of conceptual clarity. In alternative embodiments, the disclosed techniques may use other suitable configurations comprising types of connectors, such as for example receptacles and various shaped plugs. The properties of signals, the architecture and functionality of the routing circuitry may vary, such as for example the number of signal channels/frequencies the routing circuitry can convert in parallel. In an optional embodiment, signals other than ECG may be split and routed to serve as input for standalone analog instruments.

Although the embodiments described herein mainly address medical sensors, the methods and systems described herein can also be used in any other suitable application that uses sensors, including various military applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
analog-to-digital conversion (ADC) circuitry, which is coupled to digitize multiple modulated analog input signals that are modulated about different carrier frequencies so as to generate digital samples;
digital processing logic, which is configured to:
extract, from the digital samples, one or more first digital signals corresponding to a first selected subset of the analog input signals, and
one or more second digital signals corresponding to a second selected subset of the analog input signals; and
output the one or more first digital signals to a digital medical instrument; and
digital-to-analog conversion (DAC) circuitry, which is coupled to convert the one or more second digital signal into one or more analog output signals, and to output the one or more analog output signals to an analog medical instrument.

2. The apparatus according to claim 1, wherein the second selected subset comprises ECG signals, and wherein the first selected subset comprises non-ECG signals.

3. The apparatus according to claim 1, and comprising an output connector, which is configured to receive an input connector of the analog medical instrument so as to convey the one or more analog output signals to the analog medical instrument.

4. The apparatus according to claim 1, wherein the second selected subset comprises analog ECG signals, and wherein the analog medical instrument comprises an analog ECG recording instrument.

5. The apparatus according to claim 1, wherein the ADC circuitry, the digital processing logic and the DAC circuitry are integrated on a single circuit board.

6. The apparatus according to claim 1, wherein the multiple analog input signals are frequency-multiplexed onto respective carrier frequencies.

7. A method, comprising:
digitizing modulated multiple analog input signals that are modulated about different carrier frequencies so as to generate digital samples;
extracting, from the digital samples, one or more first digital signals corresponding to a first selected subset of the analog input signals, and one or more second digital signals corresponding to a second selected subset of the analog input signals;
outputting the one or more first digital signals to a digital medical instrument; and
converting the one or more second digital signal into one or more analog output signals, and outputting the one or more analog output signals to an analog medical instrument.

8. The method according to claim 7, wherein selecting the second subset of the analog input signals comprises selecting analog ECG signals, and wherein selecting the first subset of the analog input signals comprises selecting analog non-ECG signals.

9. The method according to claim 7, wherein outputting the one or more analog output signals to an analog medical instrument comprises outputting analog ECG signals to an analog ECG recording instrument.

10. The method according to claim 7, wherein digitizing multiple analog input signals comprises digitizing analog input signals that are frequency-multiplexed onto respective carrier frequencies.

11. An apparatus, comprising:
analog-to-digital conversion (ADC) circuitry, which is coupled to digitize multiple modulated analog input signals that are modulated about different carrier frequencies so as to generate digital samples;
digital processing logic, which is configured to:
split the digital samples into first and second identical copies; and
send the first copy of the digital signals to a digital medical instrument; and
output the second copy of the digital signals; and
digital-to-analog conversion (DAC) circuitry, which comprises a digital filter and is coupled to filter the second copy of the digital input signals, to convert the filtered second copy into one more analog output signals, and to output the one or more analog output signals to an analog medical instrument.

12. The apparatus according to claim 11, wherein the digital filter is configured to filter the second copy of the digital input signals by passing a first subset of the digital input signals, and dropping a second subset of the digital input signals.

13. The apparatus according to claim 12, wherein the first subset of the digital input signals comprises one or more digital ECG signals.

14. The apparatus according to claim 11, and comprising a data communication line, which is configured to transmit the second copy of digital signals to the DAC circuitry.

15. A method, comprising:
digitizing multiple modulated analog input signals that are modulated about different carrier frequencies so as to generate digital samples;
splitting the digital samples into first and second identical copies;
sending the first copy of the digital signals to a digital medical instrument;
filtering the second copy of the digital input signals by a digital filter; and
converting the filtered second copy into one more analog output signals, and
outputting the one or more analog output signals to an analog medical instrument.

16. The method according to claim 15, wherein filtering the second copy of digital signals comprises passing a first subset of the digital input signals, and dropping a second subset of the digital input signals.

17. The method according to claim 16, wherein passing the first subset of the digital input signals comprises passing one or more digital ECG signals.

18. The method according to claim 15, and comprising transmitting the second copy of digital signals using a data communication line.

* * * * *